United States Patent
Haralampopoulos et al.

(10) Patent No.: US 9,883,926 B2
(45) Date of Patent: Feb. 6, 2018

(54) CONVERSION ABUTMENT FOR DENTAL IMPLANTS

(71) Applicants: Harry A. Haralampopoulos, Oak Lawn, IL (US); Nikol H. Haralampopoulos, Oak Lawn, IL (US)

(72) Inventors: Harry A. Haralampopoulos, Oak Lawn, IL (US); Nikol H. Haralampopoulos, Oak Lawn, IL (US)

(*) Notice: Subject to any disclaimer, the term of this patent is extended or adjusted under 35 U.S.C. 154(b) by 641 days.

(21) Appl. No.: 14/206,144

(22) Filed: Mar. 12, 2014

(65) Prior Publication Data
US 2014/0272792 A1   Sep. 18, 2014

Related U.S. Application Data (60) Provisional application No. 61/799,669, filed on Mar. 15, 2013.

(51) Int. Cl.
*A61C 8/00* (2006.01)
*A61C 13/08* (2006.01)

(52) U.S. Cl.
CPC .......... *A61C 8/0068* (2013.01); *A61C 8/0016* (2013.01); *A61C 8/0048* (2013.01);
(Continued)

(58) Field of Classification Search
CPC ...... A61C 8/005; A61C 8/0069; A61C 8/0075
(Continued)

(56) References Cited

U.S. PATENT DOCUMENTS 4,687,443 A * 8/1987 Driskell ............... A61C 8/0018
433/173
4,854,872 A * 8/1989 Detsch ......................... 433/173
(Continued)

FOREIGN PATENT DOCUMENTS

EP   0685208 A1   12/1995
WO   WO 00/64369 A1   11/2000

OTHER PUBLICATIONS

Haralampopoulos HA, Haralampopoulos NH., "A Periodontal Perspective of Mini Dental Implants", JIAMDI. 2012; Fall:12-19.(as published).
(Continued)

*Primary Examiner* — Cris L Rodriguez
*Assistant Examiner* — Hao D Mai
(74) *Attorney, Agent, or Firm* — Rothwell, Figg, Ernst & Manbeck, P.C.

(57) ABSTRACT

A conversion abutment that cements onto one-piece dental implants that convert the one-piece implant use to a retrievable screw retained implant use in retaining complete dentures, hybrids, partial dentures, or fixed screw retained crowns or bridges, allowing the flexibility to retain and remove these restorative prostheses. These conversion abutments can be fabricated as angled conversion abutments to be used with single or multiple implants placed at various angulations. The conversion abutment system consists of three parts: a cementable conversion abutment (straight or angled), a coping (short or extended), and an occlusal screw. The bottom part (or apical portion) of the implant conversion abutment will cement over the one-piece implant in use, while the top (or coronal portion) will allow a screw to fit through a coping into the implant conversion abutment, screwing the prostheses into place.

16 Claims, 6 Drawing Sheets

(52) U.S. Cl.
CPC .......... *A61C 8/0053* (2013.01); *A61C 8/0075* (2013.01); *A61C 13/08* (2013.01)

(58) Field of Classification Search
USPC ........................................ 433/172–176, 201.1
See application file for complete search history.

(56) References Cited

U.S. PATENT DOCUMENTS

| | | | | |
|---|---|---|---|---|
| 4,872,839 | A * | 10/1989 | Brajnovic | 433/173 |
| 5,000,685 | A * | 3/1991 | Brajnovic | 433/173 |
| 5,006,069 | A * | 4/1991 | Lazzara | A61C 8/0048 |
| | | | | 433/173 |
| 5,069,622 | A * | 12/1991 | Rangert et al. | 433/173 |
| 5,238,405 | A * | 8/1993 | Marlin | 433/173 |
| 5,282,746 | A * | 2/1994 | Sellers | A61C 8/005 |
| | | | | 433/172 |
| 5,350,302 | A | 9/1994 | Marlin | |
| 5,368,483 | A * | 11/1994 | Sutter et al. | 433/173 |
| 5,577,912 | A * | 11/1996 | Prins | 433/172 |
| 5,662,474 | A * | 9/1997 | Jorneus et al. | 433/172 |
| 5,667,384 | A | 9/1997 | Sutter et al. | |
| 5,882,200 | A * | 3/1999 | Sutter et al. | 433/173 |
| 5,989,028 | A * | 11/1999 | Niznick | 433/173 |
| 6,244,867 | B1 * | 6/2001 | Aravena | A61C 8/005 |
| | | | | 433/172 |
| 6,250,922 | B1 * | 6/2001 | Bassett et al. | 433/172 |
| 6,663,388 | B1 * | 12/2003 | Schar et al. | 433/173 |
| 6,716,030 | B1 * | 4/2004 | Bulard | A61C 8/0048 |
| | | | | 433/174 |
| 6,824,386 | B2 * | 11/2004 | Halldin et al. | 433/173 |
| 7,108,511 | B1 | 9/2006 | Shatkin | |
| 7,217,130 | B2 * | 5/2007 | Giorno | A61C 8/0022 |
| | | | | 433/174 |
| 7,264,469 | B2 * | 9/2007 | Abarno | A61C 1/084 |
| | | | | 433/173 |
| 7,303,396 | B2 | 12/2007 | Abarno | |
| 7,699,613 | B2 * | 4/2010 | Niznick | 433/174 |
| 7,785,107 | B2 * | 8/2010 | Niznick | 433/173 |
| 8,043,089 | B2 | 10/2011 | Bulard et al. | |
| 8,118,596 | B2 * | 2/2012 | Niznick | 433/174 |
| 8,277,218 | B2 | 10/2012 | D'Alise | |
| 2003/0211445 | A1 * | 11/2003 | Klardie | A61C 8/0001 |
| | | | | 433/173 |
| 2004/0241610 | A1 * | 12/2004 | Hurson | A61C 8/0022 |
| | | | | 433/173 |
| 2006/0099549 | A1 * | 5/2006 | Engman | 433/173 |
| 2009/0117520 | A1 * | 5/2009 | Kikuchi | 433/174 |
| 2011/0117522 | A1 | 5/2011 | Verma et al. | |
| 2011/0223561 | A1 | 9/2011 | Hyun | |

OTHER PUBLICATIONS

Haralampopoulos HA, Haralampopoulos NH., "A Periodontal Perspective of Mini Dental Implants", JIAMDI. 2012; Fall:1-14.(as submitted for publication).

International Search Report and Written Opinion issued in International Application No. PCT/US2014/024506, 11 pages (dated Aug. 11, 2014).

International Preliminary Report on Patentability and Written Opinion issued in International Application No. PCT/US2014/024506, 7 pages (Sep. 15, 2015).

* cited by examiner

CONVERSION ABUTMENT FOR DENTAL IMPLANTS

PRIORITY CLAIM

This application claims the benefit under 35 U.S.C. § 119(e) of U.S. Provisional Application No. 61/799,669, filed Mar. 15, 2013, the disclosure of which is hereby incorporated by reference in its entirety.

FIELD OF THE INVENTION

The present invention relates to conversion abutments that are designed to allow dentists and dental surgeons to place, remove, replace or repair dental prostheses on one-piece dental implants.

BACKGROUND OF THE INVENTION

Individuals often find themselves requiring one or more dental prostheses during their lifetime. These prostheses can take the form of complete or partial dentures, crowns, or bridges. They may also take the form of hybrid prostheses which incorporate one or more elements of the aforementioned prostheses. Traditionally, dentistry has provided removable complete and partial dentures, crowns, and fixed bridges to solve the problem of missing teeth. To address issues associated with these traditional approaches, implant-based approaches have evolved to supplement and improve traditional prostheses. These implants may be either of the two-piece or one-piece variety. The two-piece implants have a multitude of abutment heads that can be switched to provide solutions to a variety of prosthetic situations. However, one-piece dental implants are fabricated with only one fixed head, limiting their use. One-piece dental implants, such as those with small diameters or mini dental implants, are often the only implants usable in areas of narrow bone or areas with space considerations. For a review of some advantages of mini dental implants, see "A Periodontal Perspective of Mini Dental Implants", [Haralampopoulos H A, Haralampopoulos N H. A Periodontal Perspective of Mini Dental Implants. *JIAMDI.* 2012; Fall:12-19.], which is hereby incorporated by reference in its entirety. It is known in the art that one-piece dental implants are one of the implant-based approaches often used. The one-piece dental implant provides for an abutment head on one end and a screw or fixture on the other end designed to enter the jawbone, both thereby stabilizing the attached prostheses. At least one drawback to one-piece dental implants is that one is unable to easily place, remove, repair or replace the attached prostheses without damaging the prostheses when permanently cemented, which may cause substantial discomfort and expense to the patient as well as inconvenience for both the patient and the provider.

It is the object of the present invention to provide a conversion abutment that will convert the use of a one-piece dental implant into one in which the prosthetic attachment may be affixed by screw or other securing means making the prosthesis retrievable, thus allowing for the initial placement, the removal, the repair, or the replacement of the prosthetic attachment or to provide additional fixed-retrievable prosthetic options, such as fixed-detachable hybrid prostheses, currently used in two-piece dental implant systems, but currently unavailable for one-piece dental implants, thus expanding the use of one-piece dental implants.

Existing one-piece dental implants tend to have features that make repairing, replacing or removing fixed prostheses inconvenient. For example, most commercially available implants provide for a jaw-affixed portion, the implant body, which is typically secured to the patient's jaw using a screw or cylinder with bone growing onto the surface of the implant. The two-piece implants are usually wider in diameter, usually greater than 3 mm, and may have a variety of abutment heads that can be screwed directly into the implant body, chosen to solve a variety of prosthetic treatments. The problem with one-piece dental implants is that the abutment head is not removable and can only be used in a limited choice of prosthetic treatment options. Therefore, the prostheses are attached to the abutment head portion of the jaw-affixed implant by cement or by using an abutment or part specifically designed for the one-piece abutment head. The downside to this type of construction is that permanently fixed complete and partial dentures, hybrids, crowns, and bridges cannot be easily retrieved when used with one-piece dental implants. If a prosthesis becomes damaged or worn or if an implant fails, requiring repair or replacement, one would likely have to damage or destroy the existing prosthesis in order to repair or replace the prosthesis or to have access to treat or remove a failing implant.

Currently in the prior art, there are a number of one-piece implants which are designed to allow for the implantation of various dental prostheses. For example, U.S. Pat. No. 7,108,511 discloses an implant system which comprises a mini dental implant with an abutment end. The abutment end is adapted to allow for the attachment of the dental crown of a prosthetic tooth. However, in this system, the fixation of the crown or prosthesis is performed with dental cement, and is thus permanent and irreversible without destroying the prosthesis or the dental implant itself.

U.S. Pat. No. 8,043,089 discloses a one-piece dental implant that comprises an elongated implant body that screws into the jawbone, a keeper cap which can be affixed to the implant by an O-ring-shaped insert and allows for increased stability. However, the one-piece implant described therein does not allow for a screw-based fixation to the implant body and is only used for removable prostheses.

Additional references describe various one-piece implants, including U.S. Pat. Nos. 8,118,596, 8,277,218, U.S. Pub. No. 2011/0117522 and U.S. Pub. No. 2011/0223561.

None of the above inventions and patents, taken either individually or in combination, describes the subject of the instant invention.

SUMMARY OF THE INVENTION

In one aspect of the invention, a conversion abutment is provided which is adapted to fit and/or cement onto existing one-piece dental implants converting the use to retrievable screw retained advantages currently available for two-piece dental implants. The conversion abutment may be configured to have an aperture that corresponds in shape to the head of the one-piece implant. The shapes commonly associated with heads of one-piece implants include square, rounded, or rectangular, but the conversion abutments of the present invention may be made to correspond to an implant head of any shape. These heads may be straight or tapered. Because the need sometimes arises to secure the implant into the jaw at an angle, it is also contemplated that the aperture designed to accept the head of the implant may be straight or angled. The conversion abutment may be metal, such as but not limited to titanium or zirconium, or a mixture of metals or an alloy, or polymeric or any other material known in the art to be suitable for use as an abutment.

The conversion abutment is designed to have on its top side a coronal outcropping, with a recess in its center. The recess is threaded to allow it to accept a screw.

The prosthesis, with its internal coping, is situated over the coronal outcropping of the conversion abutment. The coping may be externally or internally grooved or not grooved and internally threaded or not threaded. The internal of the coping has a lip, washer, ledge, or constriction designed to stop the occlusal screw as the screw passes through the coping and screws into the coronal outcropping of the conversion abutment. It is contemplated that the coping may be of any length—short or extended, for example—to allow for the spacing needs of the individual patient. The coping may be metal or polymeric or any other material known in the art to be suitable for use as a coping.

Through the coping is inserted an occlusal screw, which will screw through the coping, be stopped by the internal constriction, and screw into the coronal outcropping atop the conversion abutment, thus securing the coping and ultimately the prosthesis to the abutment.

In one aspect of the invention, a conversion abutment is provided for use with a one-piece wide diameter implant. In another aspect of the invention, a conversion abutment is provided for use with a one-piece narrow or small diameter implant or mini dental implant.

In another aspect of the invention, a kit is provided which comprises the conversion abutment. In a further aspect of the invention, the kit also includes the coping and/or the occlusal screw with the conversion abutment. In another aspect of the invention, the kit includes the copings and/or the occlusal screws. In yet a further aspect of the invention, the kit includes prosthetic components such as impression posts, analogs, temporary copings, and waxing sleeves to fit the conversion abutment and/or coping. In yet an even further aspect of the invention, the kit comprises an assortment of conversion abutments or multiple angled conversion abutments, each designed to fit over differently shaped or differently dimensioned implant heads.

In another aspect of the invention, an anti-rotational device can be incorporated onto various surfaces of the conversion abutment and/or the coping.

These and other features, aspects, and advantages of the present invention will become apparent to those skilled in the art after considering the following detailed description, appended claims and accompanying drawings.

DETAILED DESCRIPTION OF THE PREFERRED EMBODIMENT OF THE INVENTION

The invention will now be described in greater detail with reference to the accompanying drawings. The drawings, which are incorporated herein and form part of the specification, illustrate various, non-limiting embodiments of the present invention. In the drawings, common reference numbers indicate identical or functionally similar elements.

Unless defined otherwise, all terms of art, notations and other scientific terms or terminology used herein have the same meaning as is commonly understood by one of ordinary skill in the art to which this disclosure belongs. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

As used herein, "a" or "an" means "at least one" or "one or more."

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, inside, outside, inner, outer, internal, external, proximal, distal, in front of, behind, next to, adjacent, between, horizontal, vertical, diagonal, longitudinal, transverse, etc., are used for convenience in referring to such component, apparatus, location, feature, or a portion thereof in the drawings and are not intended to be limiting.

Furthermore, unless otherwise stated, any specific dimensions mentioned in this description are merely representative of an exemplary implementation of a device embodying aspects of the invention and are not intended to be limiting.

Figure 1:
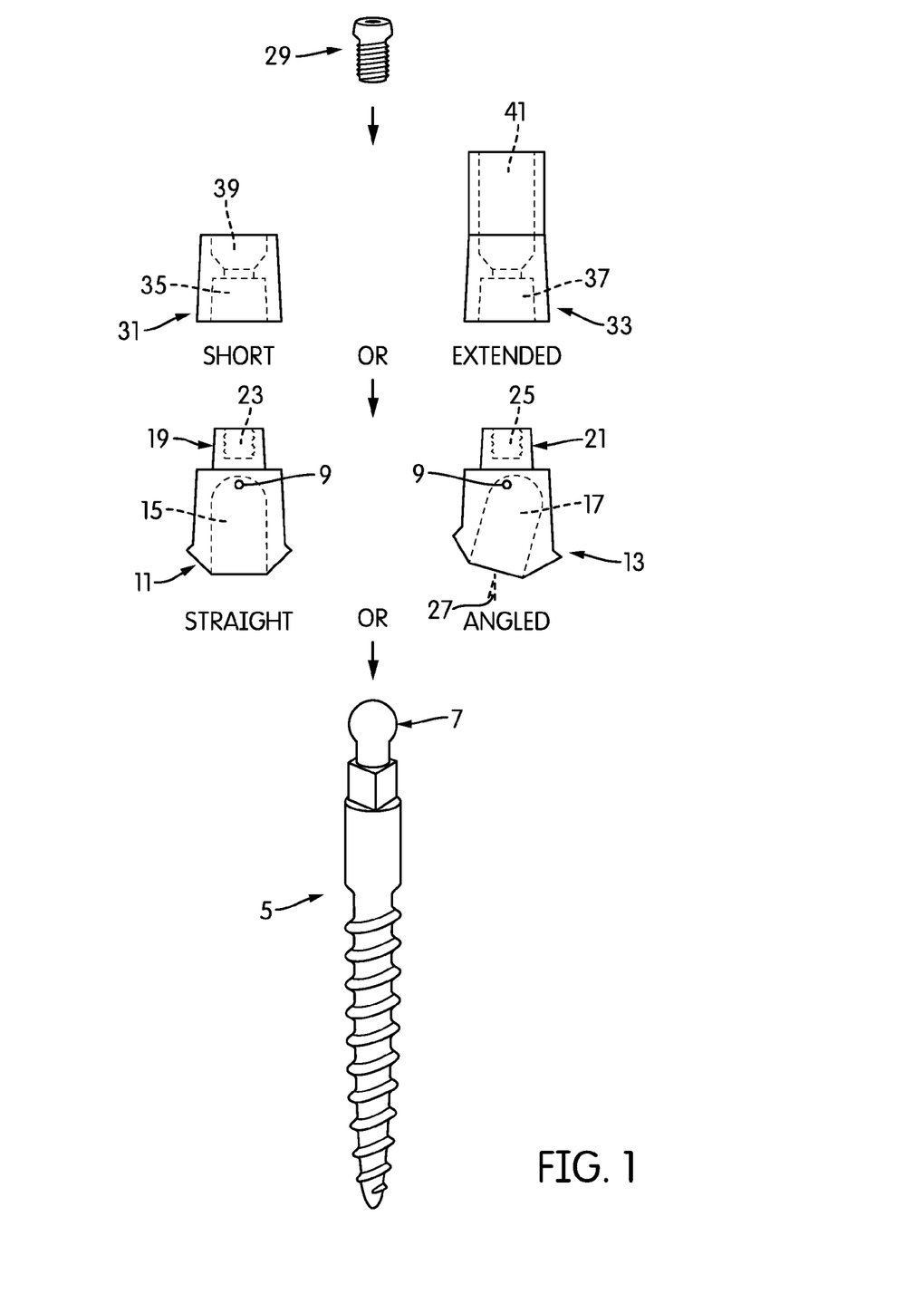
FIG. 1 is an exploded side view of the various components that comprise the conversion abutment assembly embodying aspects of the present invention.

FIG. 1 illustrates the dental implant conversion abutments, 11 and 13, embodying aspects of the present invention. The conversion abutments 11 and 13 are configured for use with one-piece dental implants, such as mini dental implants 5, which are well known in the art. It is also contemplated that the invention may be easily adapted for use with wide diameter one-piece implants (as in FIG. 6). Each conversion abutment 11 and 13, is configured to be placed over and secured, e.g., by a suitable dental cement, onto the head 7 of the one-piece implant 5 and includes a body with a substantially enclosed blind recess 15 and 17 (and further indicated by the dashed line) extending upwardly from a bottom end thereof and configured to receive the head 7 of the implant 5. Cement release holes 9 may be provided to extend from the recess 15 and 17 to permit excess cement to escape the recess when the conversion abutments 11 and 13 are placed over the head 7 of the implant 5. Each recess 15 and 17 is configured to correspond to the shape of the head 7 of the implant 5 so that the conversion abutment assembly fits snugly over the head of the implant.

Conversion abutment 11 is configured for a relatively straight installation, but, because implants must sometimes be placed into the maxilla or mandible, or otherwise installed, at an angle, an angled conversion abutment 13 is contemplated as well. Angled conversion abutment 13 allows for the adjustment of the prosthesis such that it will be occlusal facing and not appear in the mouth of the patient at the same angle as that which the implant is affixed. To accomplish this, the recess 17 of the angled conversion abutment 13, which is designed to fit over the head 7 of the implant 5, is fashioned at a tilt angle 27 relative to a longitudinal dimension extending from the bottom of the abutment 13 to the top of the abutment 13. The angles of tilt include angles of about 0° to about 45°. Angles from 0° up to about 45° are contemplated as being compatible with the present invention with the most preferred angles being 0°, approximately 15°, and approximately 30°. Additionally the gingival surface of the conversion abutment may be angled to correspond with the angle at which the implant exits the gumline.

The conversion abutment body 11 and 13 has on its top side a coronal outcropping 19 and 21, which may be externally tapered (as pictured) or straight. Each coronal outcropping 19 and 21 includes a downwardly-extending blind recess 23 and 25 which, in some embodiments, is threaded to accept an occlusal screw 29. The coronal outcropping 19 and 21 of the conversion abutment 11 and 13 is illustrated as having an approximately 15° external taper. The taper angle shown is not intended to be limiting; the taper angle may be greater or less than the angle shown. It is contemplated that the coronal outcropping may alternatively be non-tapered, partially tapered (on one or more but less than all sides and/or for less than all of its length), or fully tapered at angles of less than or more than 15°.

A dental prosthesis (not shown), will include internal coping 31 and 33 configured to be secured to the conversion abutment 11 and 13. Internal copings may be of a variety of sizes, depending on the intended installation, e.g., depending on the spacing needs of each individual patient, and FIG. 1, illustrating non-limiting exemplary embodiments, shows a "short" coping 31 and an "extended" coping 33. The coping 31 and 33 may be threaded to accept the occlusal screw 29 or non-threaded but of a diameter sufficient enough to allow for the occlusal screw to pass through the coping and into the coronal outcropping 19 or 21. The coping 31 and 33 includes an upwardly-extending recess 35 and 37 on the end that will attach to the conversion abutment 11 and 13. The coping 31 and 33 is configured to fit securely over the coronal outcropping 19 and 21 of either conversion abutment 11 and 13. The recess 35 and 37 of the coping is configured to be of the same shape, (e.g., tapered, partially tapered, or non-tapered) but slightly larger than the coronal outcropping 19 and 21 thus permitting a snug fit between the coronal outcropping 19 and 21 and the coping 31 and 33. Additionally, the surface of the coping may be of various textures and the coping may also include an undercut. The roughness of the coping surface or the inclusion of an undercut may enhance the adhesion of the prosthesis to the coping. The sizes and shapes of the copings shown are not intended to be limiting; the size and shape of the coping may be larger or smaller (and of different shape) than shown.

In one embodiment, the width of the coronal outcropping 19 and 21 of the conversion abutment 11 and 13 is less than the width of the body of the conversion abutment 11 and 13, thereby forming an upwardly facing shoulder extending at least partially about the perimeter of a base of the coronal outcropping 19 and 21. When installed onto the conversion abutment 11 and 13, a bottom portion or edge of the internal coping 31 and 33 may be supported on the upwardly facing shoulder.

Each internal coping 31 and 33 includes a corresponding bore 39 and 41, respectively. The bore 39 and 41 of the coping 31 and 33 is contemplated to extend the length of the prosthesis, such that the prosthesis can be screwed into and onto the conversion abutment 11 and 13 using the occlusal screw 29. The interior of the coping 31 and 33 has a web, a lip, washer, ledge, or constriction at the bottom of recess 39 and 41 configured to retain the occlusal screw 29 as the screw passes through the internal bore 39 and 41 of the coping and into the recess 23 and 25 of the coronal outcropping of the conversion abutment. Once installed, the screw 29 may be concealed by any material known in the art to be suitable as a filling material. Such material may include but not be limited to composite resin; acrylic; cement; gold; metal; porcelain; and/or amalgam. The length of the screw 29 shown is not intended to be limiting; the length of the screw may vary based on a variety of factors, for example, the size and shape of the coping and abutment.

Figure 2:
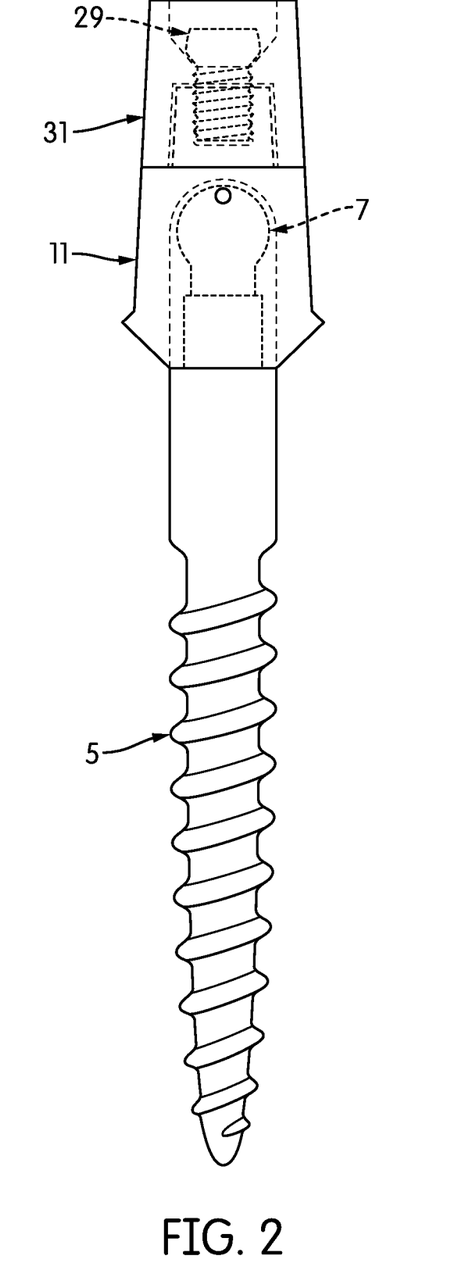
FIGS. 2 and 3 show side views of the conversion abutment assembly assembled in both its straight and angled configurations, respectively.
Figure 3:
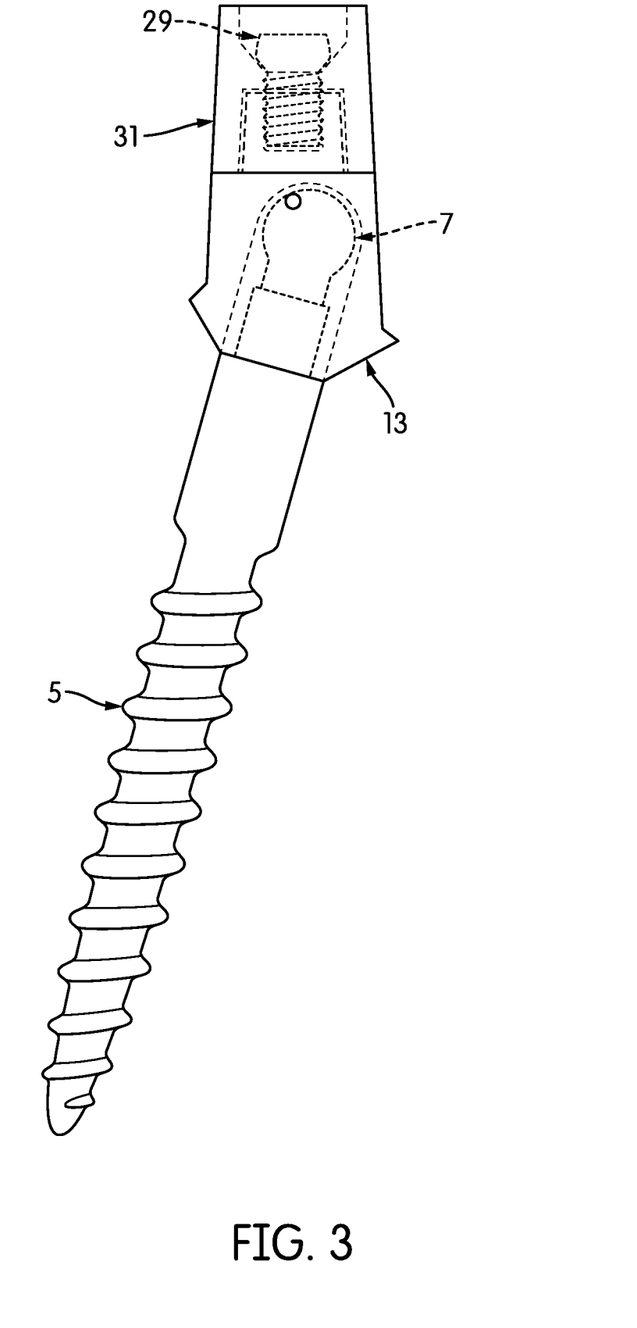

FIGS. 2 and 3 present side views of the conversion abutment and implant in its assembled state, in both the straight and angled configurations, respectively. The conversion abutment 11 and 13, is placed over the head 7 of the implant 5. The prosthesis (not shown), via its internal coping 31, is affixed to the conversion abutment 11 and 13 using an occlusal screw 29, which passes through the coping of the prosthesis and is affixed by screwing into the internally threaded coronal outcropping of the conversion abutment.

Figure 4:
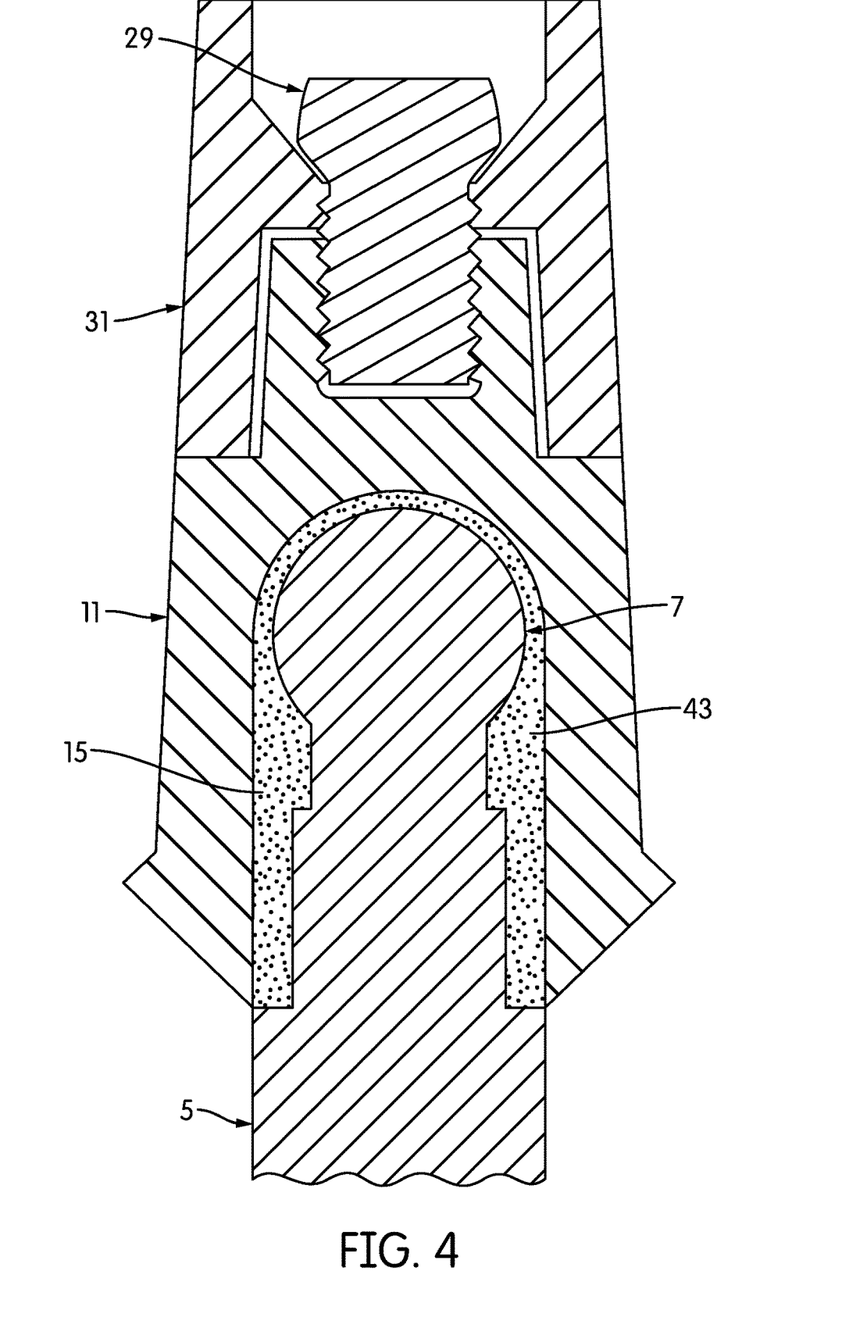
FIGS. 4 and 5 show a partial, longitudinal, cross-sectional views of the conversion abutment assembly assembled in both its straight and angled configurations, respectively, with securing cement.
Figure 5:
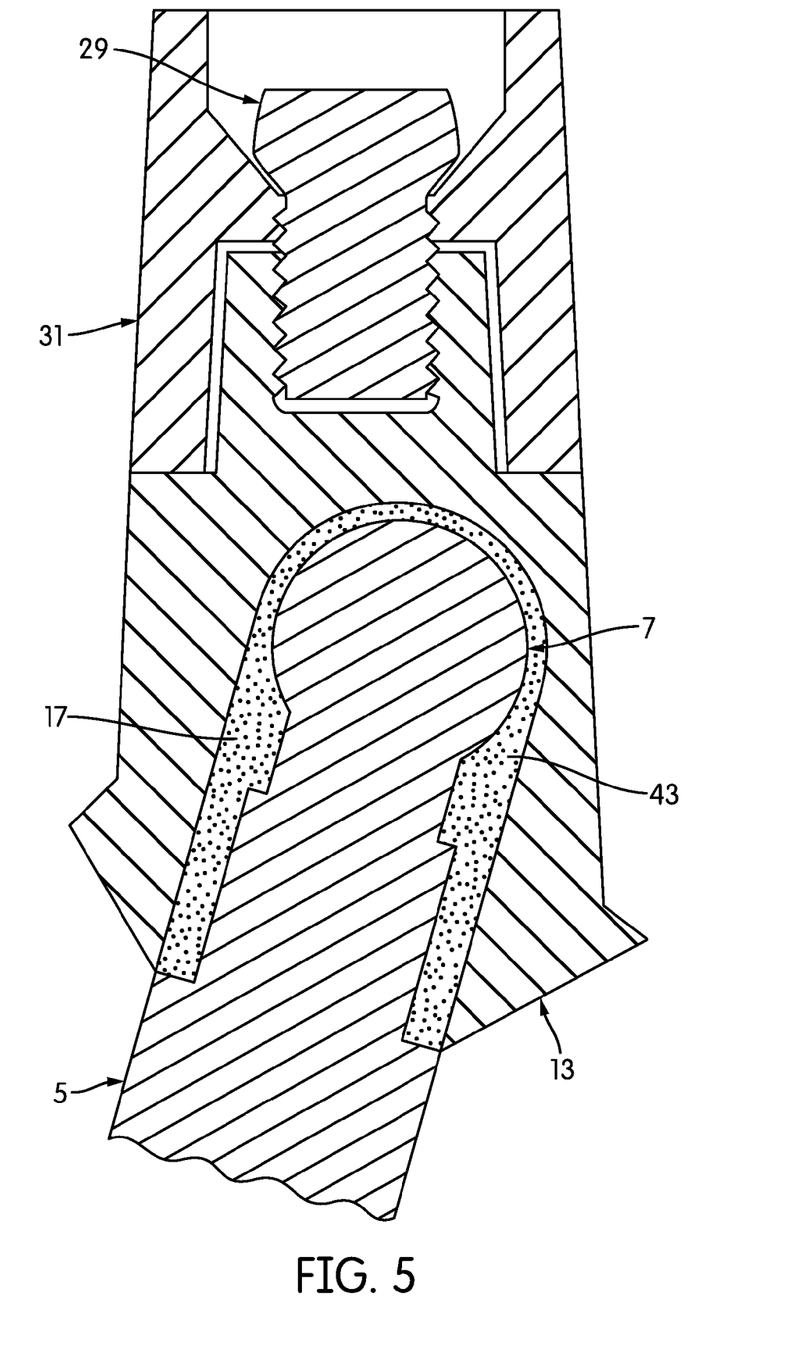

As stated above, the conversion abutment 11 and 13 is configured to be placed over and secured to the head 7 of the implant 5, e.g. by a suitable dental cement. As shown in FIGS. 4 and 5, cement 43 can be disposed between the head 7 of the implant 5 and the interior walls of recess 15 and 17, e.g. to secure the conversion abutment 11 and 13 to implant 5. Non-limiting examples of suitable cements are resin cement, composite cement, glass ionomer cement, temporary cements, and various other liquid/powder cements.

The recess of the conversion abutment may be configured to correspond to any shape of the head of an implant. The head may be spherical, such as head 5 of FIGS. 1-5. Or, as shown, for example, in an alternative embodiment of FIG. 6, recess 45 corresponds to the tapered rectangular shape of head 47. The shapes of the head of the implant shown are not intended to be limiting; the shape of the head may be different than are shown.

In another aspect of the invention, one or more anti-rotational devices (not shown) can be included to prevent rotation of the coping and/or the conversion abutment, singly or in combination. In such embodiments, an anti-rotational device, such as but not limited to, a flat side, a grooved surface, a locking-in protrusion, or arrangement can be incorporated onto, affixed to, provided on, or integrated with various surfaces of the conversion abutment and/or the coping.

Figure 6:
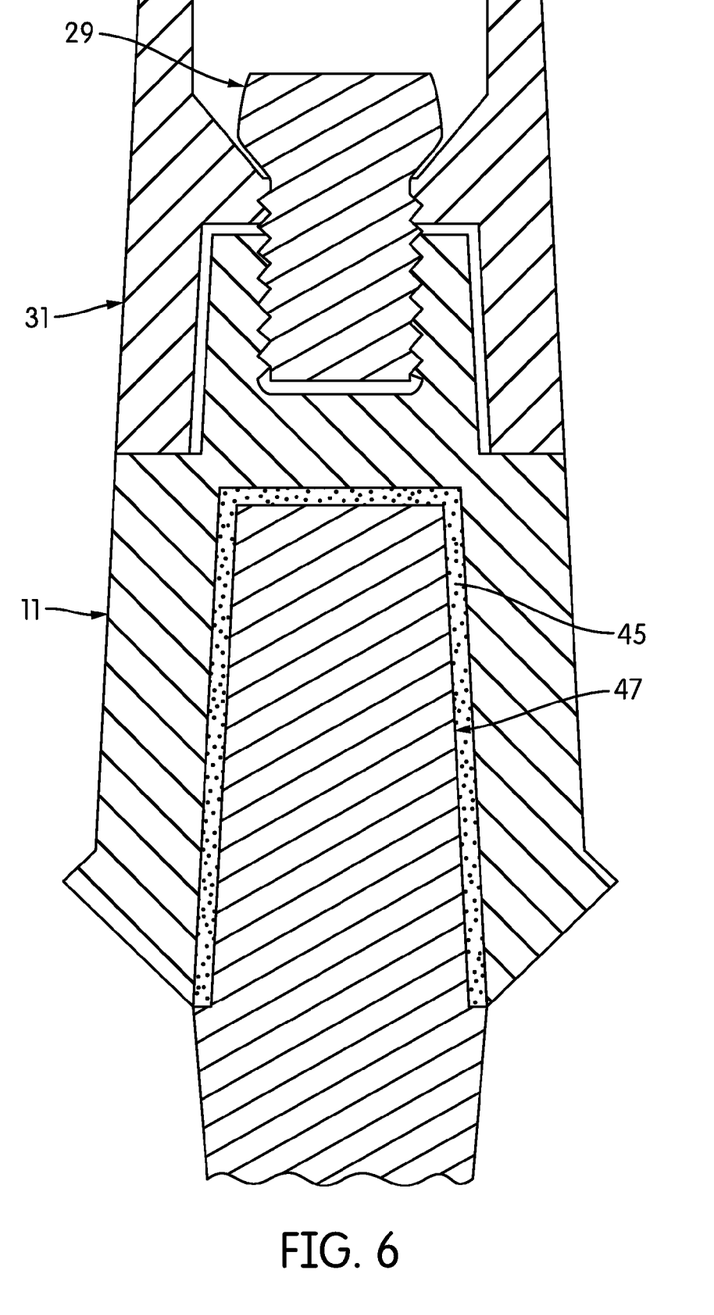
FIG. 6 shows a partial, longitudinal cross-sectional view of an alternative embodiment of the conversion abutment assembly in its straight configuration.

In another aspect of the invention, a conversion abutment is provided that is designed to fit over the head of one-piece dental implants, such as those with small diameters or mini dental implants. It is contemplated that the invention may also be used in conjunction with one-piece, wide diameter implants (FIG. 6). The invention further comprises a conversion abutment whose recess is designed to correspond in shape and dimension to the head of the implant. The coping is designed to be a hollow bore, either threaded or non-threaded. The gingival portion of the coping includes a non-tapered or tapered concavity which is designed to fit over the coronal outcropping atop the conversion abutment. An occlusal screw is provided which goes through the coping, which may or may not be threaded, engaging the coping and screwing into the internally threaded coronal feature on top of the conversion abutment.

In another aspect of the invention, an individual kit or system may be provided that comprises one or more conversion abutments with concavities that are each designed to be compatible with the heads of variously-shaped one-piece dental implants, according to the different one-piece implant designs of implant companies. The kit also comprises one or more copings around which a custom manufactured dental prosthesis may be constructed. The kit also comprises one or more occlusal screws for fixation of the prosthesis to the conversion abutment, which has been cemented onto the implant. The system includes parts and kits common to implant systems, such as but not limited to impression posts that will attach to the cementable conversion abutment to accurately capture and replicate the intraoral position of the conversion abutment and also includes but not limited to common implant prosthetic parts, such as analogs, temporary copings, prefabricated temporaries, and waxing sleeves used to fabricate dental models and dental prostheses.

While the present invention has been described and shown in considerable detail with reference to certain illustrative embodiments, including various combinations and sub-combinations of features, those skilled in the art will readily appreciate other embodiments and variations and modifications thereof as encompassed within the scope of the present invention. Moreover, the descriptions of such embodiments, combinations, and sub-combinations is not intended to convey that the inventions requires features or combinations of features other than those expressly recited in the claims. Accordingly, the present invention is deemed to include all modifications and variations encompassed within the spirit and scope of the following appended claims.

The invention claimed is:

1. A dental prosthesis assembly configured to be secured to a one-piece dental implant having a head, said assembly comprising:
   a conversion abutment comprising:
      a body having a substantially enclosed recess formed therein and configured to receive the head of the dental implant and retain a cement bond between the head of the implant and an inner surface of the recess to cementably secure the conversion abutment onto the head of the dental implant with the head of the dental implant inserted into the recess, and further comprising a cement release opening formed into the recess of the body; and
      a coronal outcropping extending from the body;
   a coping configured to be attached to said conversion abutment and including a recess formed therein for receiving said coronal outcropping of said conversion abutment; and
   a fastener element extending from said coping into said coronal outcropping for securing the coping to said conversion abutment.

2. The dental prosthesis assembly of claim 1, wherein said conversion abutment includes an upwardly-facing shoulder for supporting the coping.

3. The dental prosthesis assembly of claim 1, wherein said fastener element comprises an occlusal screw.

4. The dental prosthesis assembly of claim 1, wherein said coronal outcropping has a blind threaded hole formed into a top end thereof and the fastener element comprises a screw extending from said coping into the threaded hole of the coronal outcropping.

5. The dental prosthesis of claim 4, wherein the threaded hole and the recess for receiving the head of the dental implant are substantially aligned.

6. The dental prosthesis of claim 4, wherein the recess for receiving the head of the dental implant is at an angle relative to the threaded hole formed in the coronal outcropping to accommodate a dental implant installed at an angle.

7. The dental prosthesis assembly of claim 1, wherein the coping is constructed of metal.

8. The dental prosthesis assembly of claim 1, wherein the coping is constructed of plastic.

9. A dental prosthesis kit comprising:
   a plurality of conversion abutments, wherein each of said plurality of conversion abutments is configured to be secured to a one-piece dental implant having a head;
   at least one coping configured to be attached to one of said plurality of conversion abutments, said at least one coping including a recess formed therein; and
   at least one fastener element;
   wherein each of said plurality of conversion abutments comprises:
   a body having a substantially enclosed recess formed therein and configured to receive the head of the dental implant and retain a cement bond between the head of the dental implant and an inner surface of the recess of the body to cementably secure the conversion abutment onto the head of the dental implant;
   a cement release opening formed into the recess of the body; and
   a coronal outcropping extending from the body and configured to be inserted into the recess of the coping and to enable the coping to be removably attached to the coronal outcropping of the conversion abutment with the fastener element extending from the coping and into a recess of the coronal outcropping, wherein each body is adapted for use with a different-shaped implant head.

10. The kit of claim 9, wherein said plurality of conversion abutments comprising at least one of a straight conversion abutment and an angled conversion abutment; wherein the kit further comprises dental prosthesis assembly components for use with either of said at least one of said straight or angled conversion abutments.

11. The kit of claim 9, wherein said at least one coping comprises at least one of a short coping and an extended coping.

12. The kit of claim 9, comprising one or more prostheses configured for use with one or more of the plurality of conversion abutments.

13. The dental prosthesis assembly of claim 1, wherein said coronal outcropping has a smaller width than said body.

14. The dental prosthesis assembly of claim 1, wherein said coronal outcropping is tapered.

15. The kit of claim 9, wherein said coronal outcropping has a smaller width than said body.

16. The kit conversion abutment of claim 9, wherein said coronal outcropping is tapered.

* * * * *